Feb. 16, 1960 D. H. MOREY, JR Plant Pat. 1,908
ROSE PLANT
Filed May 25, 1959
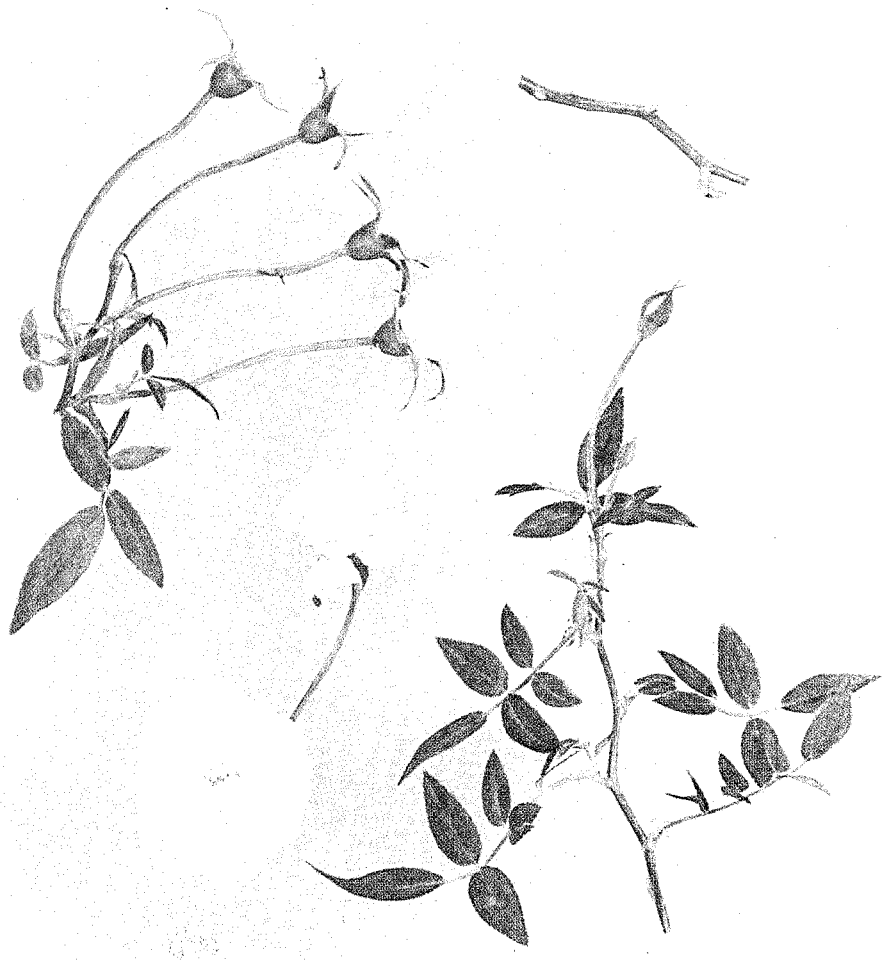
Inventor.
D. H. Morey, Jr.
By: Robb & Robb
Attorneys.

United States Patent Office

Plant Pat. 1,908
Patented Feb. 16, 1960

1,908

ROSE PLANT

Dennison H. Morey, Jr., Pleasanton, Calif., assignor to Jackson & Perkins Company, Newark, N.Y., a corporation of New York Application May 25, 1959, Serial No. 815,761

1 Claim. (Cl. 47—61)

The present invention relates to a new and distinct variety of rose plant of the miniature class, which was originated by me by crossing an unnamed and unpatented sport of "Dick Koster" (unpatented) with the variety "Tom Thumb" (Plant Patent No. 169), said latter variety also being known in Europe as "Peon."

The primary objective of this breeding was to produce a new variety of miniature rose having a low-growing habit and which bears flowers of a color acceptable for general use. This objective was fully achieved, along with other desirable improvements, as evidenced by the following unique combination of characteristics which are outstanding in the new variety and which distinguish it from its parents, as well as from all other varieties of which I am aware:

(1) A low-growing plant habit (averaging from 6 to 8 inches tall), with a somewhat more open structure than other miniature varieties;

(2) Attractive, perfectly formed miniature buds and the double form of the flowers when fully open;

(3) The miniature size of the flowers, averaging from ½ to ¾ inches in diameter; and (4) A distinctive general color tonality of the flowers corresponding to White faintly overcast with Hermosa Pink.

Asexual reproduction of the new variety by own-rooted cuttings, as performed at Pleasanton, California, and also at Newark, New York shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—An unnamed sport of "Dick Koster."
*Pollen parent.*—"Tom Thumb."

Classification:
*Botanic.*—Hybrid chinensis minima.
*Commercial.*—Miniature.

*Flower*

(Observations made from specimens grown in a greenhouse at Newark, New York in the early afternoon during the middle of December.)

Blooming habit: Recurrent—intermittent.

Bud:
*Size.*—Very small.
*Form.*—Globular; is not affected by wet or hot weather.
*Color.*—When sepals first divide—Hermosa Pink, Plate 1. When petals begin to unfurl—White, Plate 53, with edge of petals overcast with Hermosa Pink, Plate 1. When half-blown: inside of petals—White, Plate 53, lightly overcast with Pale Vinaceous Pink, Plate 28; reverse of petals—White, Plate 53, with outer edge of petals lightly overcast with Cameo Pink, Plate 26.
*Sepals.*—Slightly branched; curl back when petals begin to unfurl. Color: inside—Light Grape Green, Plate 41; outside—Cress Green, Plate 31.
*Calyx.*—Color—Cress Green, Plate 31. Shape—pear. Size — small. Aspect — smooth. Odor when rubbed—none.
*Peduncle.*—Length—short. Aspect—smooth. Strength — erect; slender. Color — Asphodel Green, Plate 4.
*Opening.*—Opens up well; is not affected by adverse weather conditions.

Bloom:
*Size.*—Small. Average size when fully expanded —from ½ to ¾ inch.
*Borne.*—Several together, and in irregular clusters.
*Stems.*—Short; normal strength.
*Form (when first open).*—Cupped. Permanence—flattens; outer petals curl back.
*Petalage.*—Double (full but open center). Number of petals under normal conditions—from 45 to 50.
*Color.*—Center of flower—White, Plate 53, with edge of petals lightly overcast with Hermosa Pink, Plate 1. Outer petals—White, Plate 53, with edge of petals faintly overcast with Hermosa Pink, Plate 1. Base of petals (aiglet)—Glass Green, Plate 31. Inside of petals—White, Plate 53, faintly overcast with Hermosa Pink, Plate 1. Reverse of petals—White, Plate 53. General tonality from a distance—White, Plate 53, faintly overcast with Hermosa Pink, Plate 1, on the outer edge of the petals.
*Discoloration.*—General tonality at end of first day —White, Plate 53, lightly overcast with Hermosa Pink, Plate 1. Second day—White, Plate 53, lightly overcast with Hermosa Pink, Plate 1. Third day—White, Plate 53.

Petals:
*Texture.*—Thin; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Small; few; regularly arranged around styles. Color—Pale Greenish Yellow, Plate 5.
Stamens, filaments (threads): Short. Color—Sea-foam Yellow, Plate 31.
Pollen: Color—Sulphur-Yellow, Plate 5.
Styles: Columnar; uneven length; short; thin.
Stigmas: Color—Sea-foam Yellow, Plate 31.
Ovaries: All enclosed in calyx.
Hips: None.
Seeds: None.

*Plant*

Form: Bush; from 6 inches to 8 inches tall.
Growth: Medium; dwarf; open.

Foliage: Compound of 5 to 7 leaflets.

*Size.*—Small.

*Quantity.*—Normal.

*Color.*—New foliage: upper side—Light Bice Green, Plate 17; under side—Light Cress Green, Plate 31. Old foliage: upper side—Dark Cress Green, Plate 31; under side—Cress Green, Plate 31.

*Shape.*—Oval pointed.

*Texture.* — Upper side — glossy. Under side—smooth.

*Ribs and veins.*—Light.

*Edge.*—Serrated (saw toothed).

*Serration.*—Single; small.

*Leaf stem.*—Color—Absinthe Green, Plate 31. Under side—smooth.

*Stipules.*—Short; bearded.

Wood:

*New wood.*—Color—Light Cress Green, Plate 31. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; short; straight. Color (when young)—Turtle Green, Plate 32. Position—irregular.

*Prickles.*—Quantity: on main stalks—none; on laterals—none.

*Short needles.*—Quantity: on main stalks—none; on laterals—none.

I claim:

A new and distinct variety of rose plant of the miniature class, substantially as herein shown and described, characterized particularly as to novelty by the unique combination of a low-growing and open plant habit, perfect form of miniature buds and double form of the fully open flowers, said flowers being of miniature size, and a distinctive general color tonality of the flowers corresponding to White, faintly overcast with Hermosa Pink.

No references cited.